United States Patent
Schmitt et al.

(10) Patent No.: US 10,898,267 B2
(45) Date of Patent: Jan. 26, 2021

(54) MOBILE FFR SIMULATION

(71) Applicant: KONINKLIJKE PHILIPS N.V., Eindhoven (NL)

(72) Inventors: Holger Schmitt, Luetjensee (DE); Christian Haase, Hamburg (DE); Hannes Nickisch, Hamburg (DE); Sven Prevrhal, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 367 days.

(21) Appl. No.: 15/760,649

(22) PCT Filed: Sep. 26, 2016

(86) PCT No.: PCT/EP2016/072787
§ 371 (c)(1),
(2) Date: Mar. 16, 2018

(87) PCT Pub. No.: WO2017/060106
PCT Pub. Date: Apr. 13, 2017

(65) Prior Publication Data
US 2019/0038356 A1 Feb. 7, 2019

(30) Foreign Application Priority Data
Oct. 7, 2015 (EP) ..................... 15188699

(51) Int. Cl.
*H04N 9/47* (2006.01)
*A61B 34/10* (2016.01)
(Continued)

(52) U.S. Cl.
CPC ............ *A61B 34/10* (2016.02); *A61B 5/0033* (2013.01); *A61B 5/02007* (2013.01);
(Continued)

(58) Field of Classification Search
CPC ......... A61B 34/10; A61B 5/742; A61B 5/055; A61B 6/032; A61B 6/461; A61B 6/504;
(Continued)

(56) References Cited

U.S. PATENT DOCUMENTS 8,157,742 B2   4/2012   Taylor
8,200,466 B2   6/2012   Spilker
(Continued)

FOREIGN PATENT DOCUMENTS

DE   102008014792   6/2009
JP   2005216011    8/2005
(Continued)

OTHER PUBLICATIONS

Wink, et al., "Multiscale vessel tracking", IEEE Transactions on Medical Imaging, vol. 23, No. 1, Jan. 2004.
(Continued)

*Primary Examiner* — Robert Chevalier
(74) *Attorney, Agent, or Firm* — Larry Liberchuk

(57) ABSTRACT

Stenosis information is obtained by obtaining photographic image data (302) from a displayed image of a blood vessel (103, 203) containing the stenosis. Contours of the blood vessel and the stenosis are detected and dimensions are estimated from the photographic image data. A blood vessel model is reconstructed and fractional flow reserve data is calculated using the blood vessel model.

15 Claims, 3 Drawing Sheets

(51) Int. Cl.

| | | |
|---|---|---|
| *A61B 6/03* | (2006.01) | |
| *A61B 6/00* | (2006.01) | |
| *A61B 5/00* | (2006.01) | |
| *G16H 50/50* | (2018.01) | |
| *A61B 5/02* | (2006.01) | |
| *G16H 30/40* | (2018.01) | |
| *G06T 7/13* | (2017.01) | |
| *A61B 5/055* | (2006.01) | |
| *G06T 7/60* | (2017.01) | |
| *A61B 5/021* | (2006.01) | |
| *A61B 5/026* | (2006.01) | |
| *G06T 7/70* | (2017.01) | |
| *G06T 17/00* | (2006.01) | |
| *H04N 5/225* | (2006.01) | |

(52) U.S. Cl.
CPC .......... *A61B 5/055* (2013.01); *A61B 5/6898* (2013.01); *A61B 5/7278* (2013.01); *A61B 5/742* (2013.01); *A61B 5/7425* (2013.01); *A61B 6/032* (2013.01); *A61B 6/461* (2013.01); *A61B 6/503* (2013.01); *A61B 6/504* (2013.01); *A61B 6/507* (2013.01); *G06T 7/13* (2017.01); *G06T 7/60* (2013.01); *G16H 30/40* (2018.01); *G16H 50/50* (2018.01); *A61B 5/021* (2013.01); *A61B 5/026* (2013.01); *A61B 6/4417* (2013.01); *A61B 6/462* (2013.01); *A61B 2034/105* (2016.02); *G06T 7/70* (2017.01); *G06T 17/00* (2013.01); *G06T 2200/08* (2013.01); *G06T 2207/10004* (2013.01); *G06T 2207/10081* (2013.01); *G06T 2207/10088* (2013.01); *G06T 2207/10116* (2013.01); *G06T 2207/20024* (2013.01); *G06T 2207/20092* (2013.01); *G06T 2207/30104* (2013.01); *H04N 5/225* (2013.01)

(58) Field of Classification Search
CPC ..... A61B 6/507; A61B 2034/105; G06T 7/13; G06T 7/60; G06T 7/70; G06T 2207/30104; G06T 2207/10004; G06T 2207/10081; G06T 2207/10088; G06T 2207/10116
USPC .............. 348/77, 79, 80, 121, 135, 137, 143
See application file for complete search history.

(56) References Cited

U.S. PATENT DOCUMENTS

| | | | |
|---|---|---|---|
| 8,249,815 B2 | 8/2012 | Taylor | |
| 8,594,950 B2* | 11/2013 | Taylor | A61B 6/504 702/19 |
| 9,087,147 B1* | 7/2015 | Fonte | A61B 6/503 |
| 2004/0114717 A1 | 6/2004 | Kato | |
| 2010/0125197 A1 | 5/2010 | Fishel | |
| 2010/0130878 A1 | 5/2010 | Lasso | |
| 2010/0241404 A1 | 9/2010 | Taylor | |
| 2011/0211742 A1 | 9/2011 | Bredno | |
| 2011/0307231 A1 | 12/2011 | Kirchner | |
| 2012/0022843 A1 | 1/2012 | Ionasec | |
| 2012/0041318 A1 | 2/2012 | Taylor | |
| 2012/0041319 A1 | 2/2012 | Taylor | |
| 2012/0041320 A1 | 2/2012 | Taylor | |
| 2012/0041321 A1 | 2/2012 | Taylor | |
| 2012/0041322 A1 | 2/2012 | Taylor | |
| 2012/0041323 A1 | 2/2012 | Taylor | |
| 2012/0041324 A1 | 2/2012 | Taylor | |
| 2012/0041325 A1 | 2/2012 | Taylor | |
| 2012/0041739 A1 | 2/2012 | Taylor | |
| 2012/0053919 A1 | 3/2012 | Taylor | |
| 2012/0059246 A1 | 3/2012 | Taylor | |
| 2012/0072190 A1 | 3/2012 | Sharma | |
| 2012/0121151 A1 | 5/2012 | Bernhardt | |
| 2012/0243761 A1 | 9/2012 | Senzig | |
| 2012/0296199 A1 | 11/2012 | Kim | |
| 2013/0314388 A1 | 11/2013 | Oda | |
| 2014/0024932 A1 | 1/2014 | Sharma | |
| 2014/0114618 A1 | 4/2014 | Fonte | |
| 2014/0249399 A1 | 9/2014 | Sharma | |
| 2015/0089337 A1 | 3/2015 | Grady | |

FOREIGN PATENT DOCUMENTS

| | | |
|---|---|---|
| JP | 2006198296 | 8/2006 |
| KR | 101258961 | 4/2013 |
| WO | 00/72037 | 11/2000 |
| WO | 2004025572 | 3/2004 |
| WO | 200661814 | 6/2006 |
| WO | 200661815 | 6/2006 |
| WO | 201022762 | 3/2010 |

OTHER PUBLICATIONS

Frangi, et al., "Multiscale Vessel Enhancement Filtering", Proc. Medical Image Computing and Computer-Assisted Intervention, 1998, Springer, pp. 130-137.

Haase et al., "Quantification of intracoronary volume by videodensitometry: Validation study using fluid filling of human coronary casts", Catheterization and Cardiovascular Diagnosis, vol. 33, No. 1, pp. 89-94, 1994.

Van de Vosse, "Mathematical modelling of the cardiovascular system", Journal of Engineering Mathematics, vol. 47, pp. 175-183, 2003.

Kim et al., "Patient-specific modeling of blood flow and pressure in human coronary arteries", Annals of Biomedical Engineering, vol. 38, No. 10, pp. 3195-3209, 2010.

Smith et al., "An anatomically based model of transient coronary blood flow in the heart", SIAM Journal on Applied Vlathematics, vol. 62, No. 3, pp. 990-1018, 2001.

* cited by examiner

MOBILE FFR SIMULATION

CROSS REFERENCE TO RELATED APPLICATIONS

This application is the U.S. National Phase application under 35 U.S.C. § 371 of International Application No. PCT/EP2016/072787, filed Sep. 26, 2016, published as WO 2017/060106 on Apr. 13, 2017, which claims the benefit of European Patent Application Number 15188699.1 filed Oct. 7, 2015. These applications are hereby incorporated by reference herein.

FIELD OF THE INVENTION

The present invention generally relates to a method for obtaining stenosis information in a blood vessel comprising a stenosis, a portable mobile device and a computer program for obtaining stenosis information in a blood vessel comprising a stenosis.

BACKGROUND OF THE INVENTION

Traditionally, a stenosis (a lesion that forms a narrowing of a blood vessel) and its impact on blood flow is detected by catheterization, which measures pressure in the blood vessel before (proximal to) and behind (distal to) the stenosis. From the pressure measurements a fractional flow reserve (FFR) is calculated, which is the most used property to determine functional stenosis severity.

Recently non-invasive image-based stenosis detection and characterization methods have become available as well. These image-based methods are performed using 3D coronary artery models extracted from image volumes obtained by 3D imaging, for instance computed tomography (CT) imaging and usually will provide simulated FFR values.

Known image-based models require a high computational effort and are in some cases time consuming.

SUMMARY OF THE INVENTION

The present invention attempts to provide a simpler and less time consuming non-invasive alternative to the known FFR determination methods and systems.

Embodiments according to the present invention are directed to a method for obtaining stenosis information in a blood vessel comprising a stenosis. The method comprises the steps of displaying an initial image of an area of interest of a patient comprising at least the stenosis on a display unit; obtaining photographic data of the displayed image of the area of interest using a camera of a portable mobile device; estimating a blood vessel size from the photographic data; detecting contours of at least the blood vessel and the stenosis; reconstructing a blood vessel model based on the obtained photographic image data and the detected contours; simulating blood pressure values and blood flow values in the blood vessel proximal to and distal to the stenosis using at least the blood vessel model and the estimated blood vessel size; calculating a fractional flow reserve value from the simulated blood pressure values and blood flow values; and displaying the calculated fractional flow reserve value. In other words: a photograph is taken of the displayed image and a portable mobile device is used to analyze the image and determine the FFR values. As such, stenosis information is quickly and with low computational power by using a portable mobile device.

A preferred embodiment includes that wherein the initial image of the area of interest was obtained by 2D or 3D medical imaging data, preferably chosen from a group comprising X-ray imaging data, computed tomography imaging data or magnetic resonance imaging data. Such imaging data is of high quality and may form a good basis to obtain stenosis information from.

A further preferred embodiment includes that the blood vessel is displayed in an orientation such that an unobstructed view of the stenosis is displayed. This ensures that the stenosis data is accurate.

A further preferred embodiment includes that the photographic data comprises a still image or a series of still images. The still image may be manually or automatically selected from a series of still images.

A further preferred embodiment includes that the photographic data comprises temporal information relating to a time frame in which the photographic data was obtained and/or positional information relating to a spatial position in which the photographic data was obtained. This additional data may be used as input for reconstruction, modeling or calculation algorithms to obtain more accurate stenosis information with respect to a position or time frame.

A further preferred embodiment includes that the blood vessel size is estimated by detecting known structures in the photographic image data; comparing the detected known structures to typical dimensions of the known structures; and calculating a scale factor based on the compared dimensions. This is an automated procedure that may be performed quickly.

A further preferred embodiment includes that the blood vessel size was estimated or influenced by a user-defined scale factor. A user may define or correct the size by using his knowledge on interpreting medical images.

A further preferred embodiment includes that the contours of the blood vessel and/or the stenosis are automatically determined, preferably by a vesselness filter. Alternatively, the contours may be manually determined by a user or the automatic determination may be influenced or corrected by a user.

A further preferred embodiment includes that the calculated fractional flow reserve value are displayed as a single value distal to the stenosis or as a color coded pressure gradient along the blood vessel.

A further preferred embodiment includes that also a recommendation for further investigation is displayed.

Other, corresponding embodiments are directed towards a portable mobile device and a computer program product configured to perform the relevant steps of the method with.

Still further aspects and embodiments of the present invention will be appreciated by those of ordinary skill in the art upon reading and understanding the following detailed description. Numerous additional advantages and benefits will become apparent to those of ordinary skill in the art upon reading the following detailed description of preferred embodiments.

The invention may take form in various components and arrangements of components, and in various process operations and arrangements of process operations. The drawings are only for the purpose of illustrating preferred embodiments and are not to be construed as limiting the invention. To better visualize certain features may be omitted or dimensions may be not according to scale.

DETAILED DESCRIPTION OF EMBODIMENTS

In radiology and cardiology departments, blood vessels, such as for instance coronary arteries, as imaged by imaging systems, such as for instance 3D x-ray, computed tomography (CT), magnetic resonance (MR), positron emission transmission (PET), single-photon emission computed tomography (SPECT), ultrasound (US) or combinations thereof, are displayed on screens with the intention to measure and assess the severity of a stenosis. The most common way to express stenosis severity is fractional flow reserve (FFR), which is defined as the ratio of maximum blood flow distal to a stenotic lesion in a blood vessel to normal maximum flow in the same vessel: FFR=Pd/Pa (Pd is the pressure distal to the lesion, Pa is the pressure proximal to the lesion).

The blood pressure may be measured in the artery using catheterization, but it may also be simulated using advanced models that analyze the imaging data and calculate simulated FFR (and/or other related blood flow or pressure) values. Depending on the used model and required accuracy, calculation of the FFR values may take between minutes and hours. However, processing time will reduce further with more advanced computational power and further improved models.

Normally, FFR is modeled using 3D image data, but recently it has become possible to also use 2D image data, such as 2D contrast-enhanced angiographic data. Under the right conditions (e.g. an unobstructed view of the stenosis and an optimal orientation of the blood vessel), FFR calculations may be obtained without the need to extract the full coronary tree and therefore require significantly less computational power. This insight lies at the basis of the present invention.

The present invention proposes to take the 2D approach further and simulate FFR values on portable mobile devices which use their built-in camera to capture the geometry of blood vessels and stenoses from any suitable display of medical imaging devices.

Current 3D models are complex and require high computational power and direct access to the original 3D image data. It is therefore the obvious choice to use a strong computer that is integrated in or directly connected to the imaging device to perform the modelling and the FFR calculations. A skilled person would not use a small mobile device to perform this task, but the inventive insight that 2D modeling, when done right, lowers the requirements for computational power such that becomes available for less powerful devices, such as mobile phones.

Figure 1:
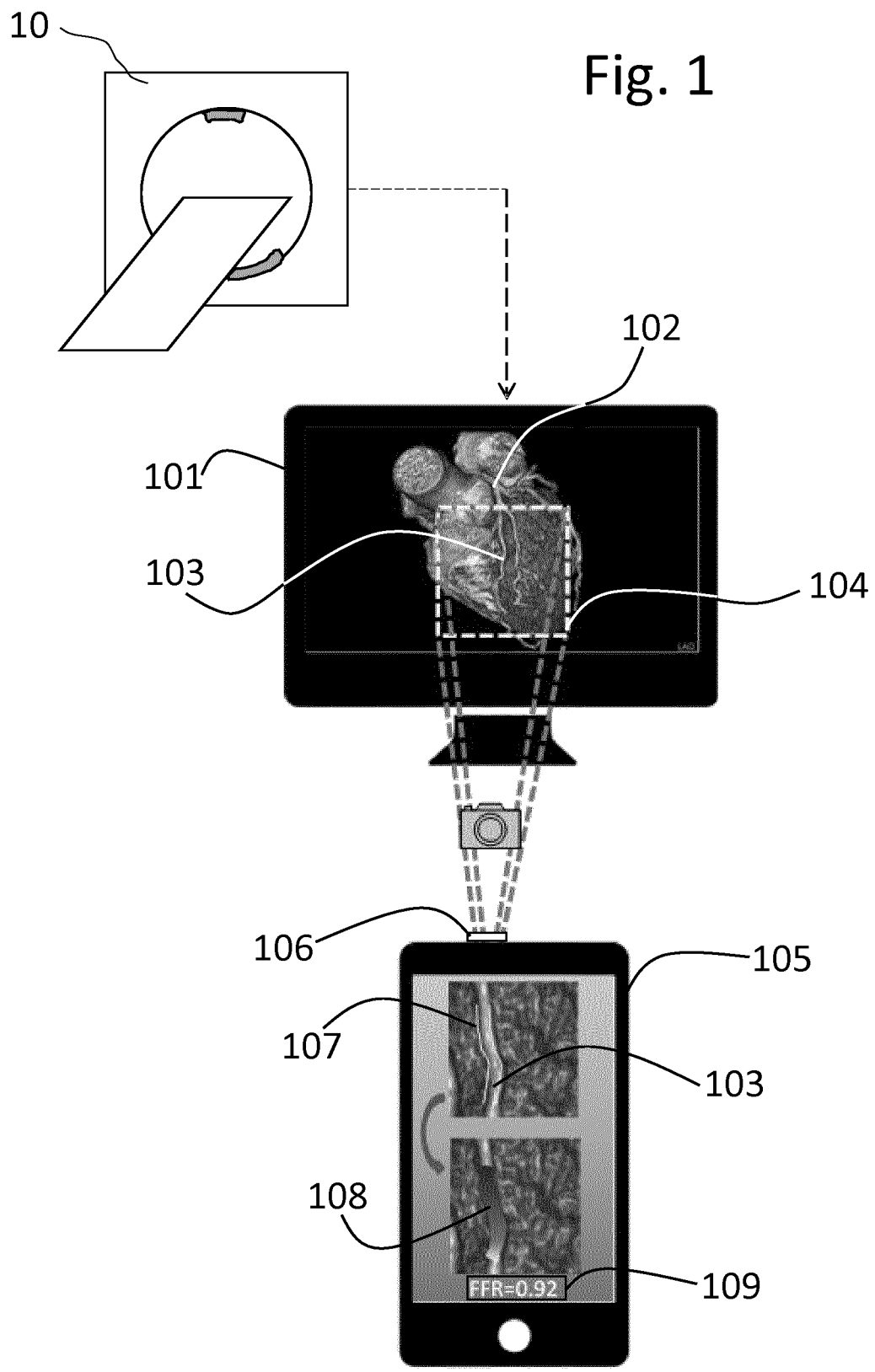
FIG. 1 shows a schematic depiction of an embodiment of a method and device of the present invention using a 3D computed tomography image as an initial image.
Figure 2:
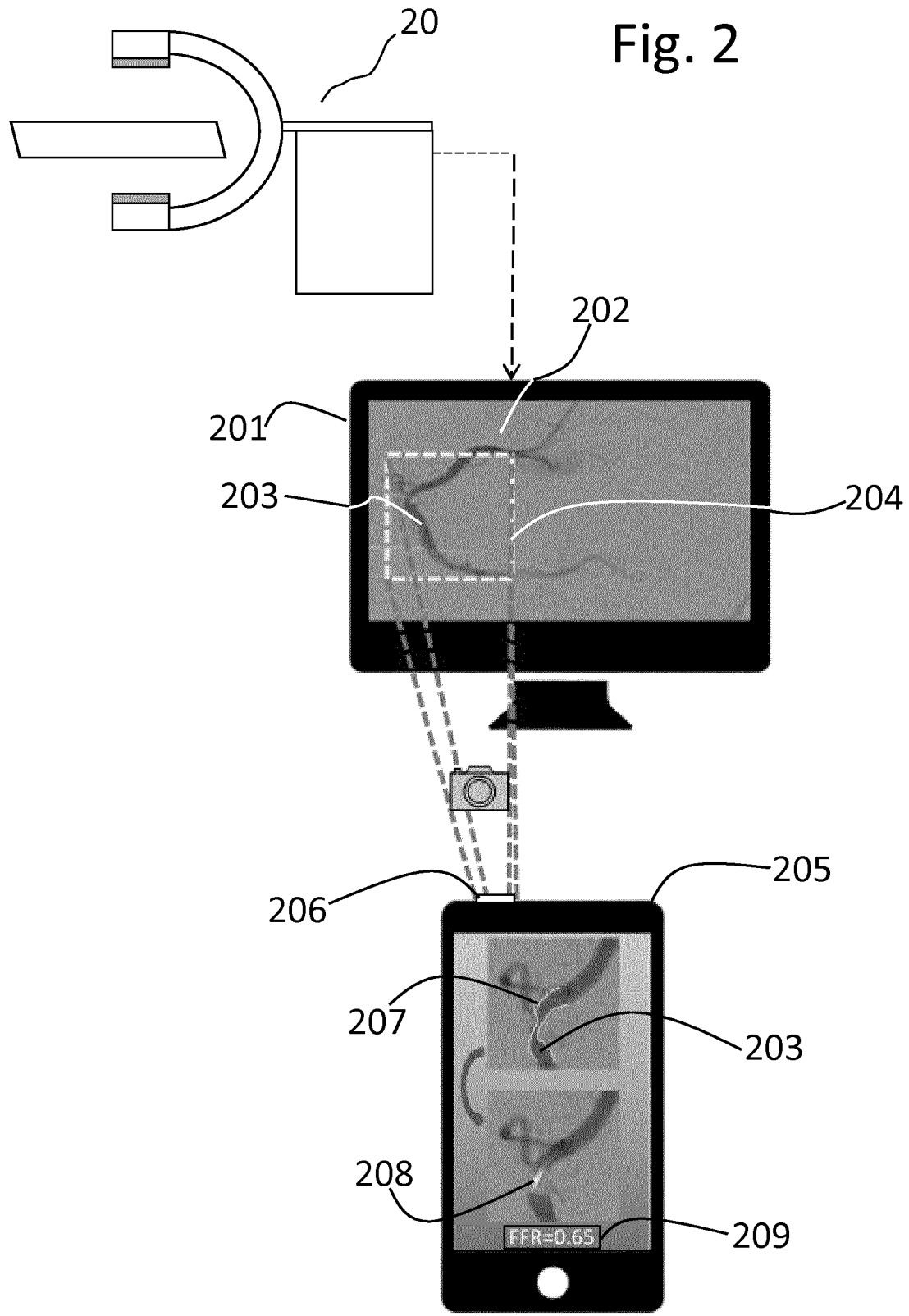
FIG. 2 shows a schematic depiction of an embodiment of a method and device of the present invention using a 2D X-ray image as an initial image.
Figure 3:
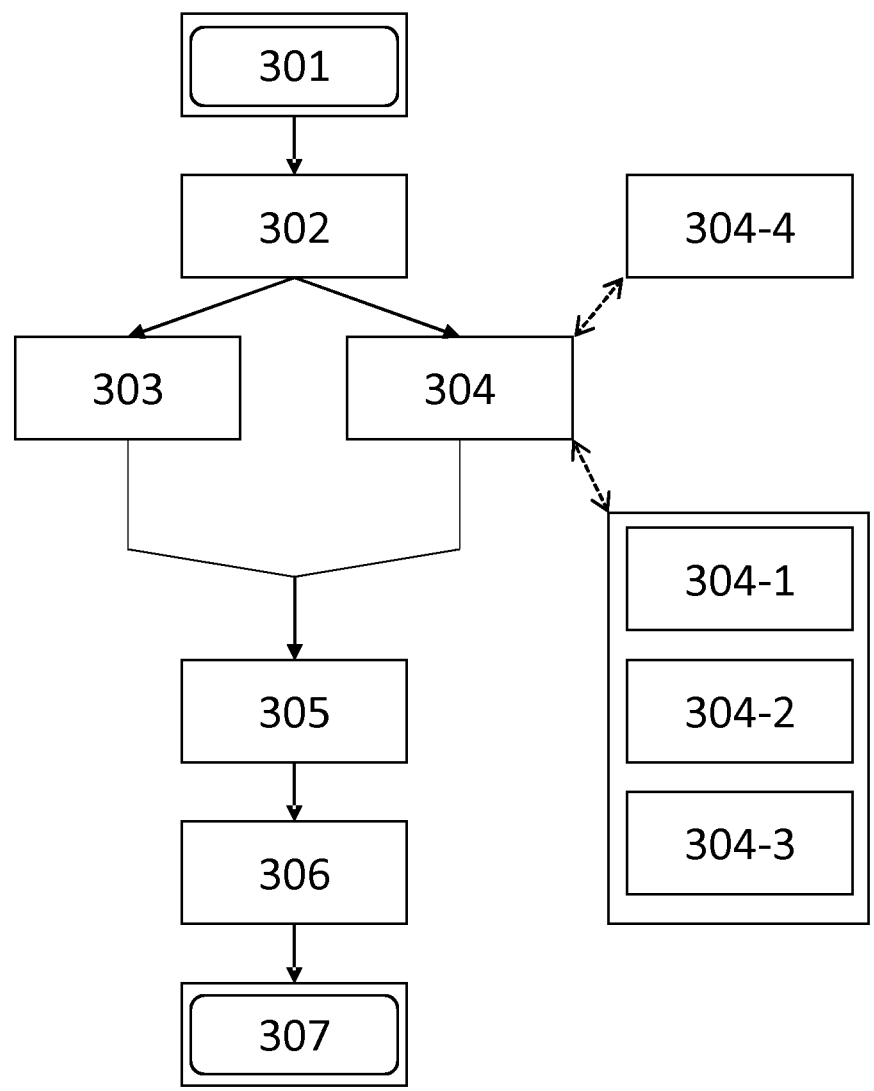
FIG. 3 shows a flowchart of an embodiment of a method according to the present invention.

FIGS. 1, 2 and 3 all illustrate the present invention and how it may be implemented. Of course, a skilled person would understand that the present invention may be implemented in different embodiments as well to achieve the same or similar result. FIGS. 1 and 2 show a schematic depiction of an embodiment of the present invention using a 3D computed tomography (FIG. 1) and a 2D X-ray (FIG. 2) image respectively as an initial image. FIG. 3 shows a flowchart of a workflow according to the present invention.

First an initial image is obtained and displayed 301, for instance an image of an organ, such as a heart or a cardiac arterial system, or a section of a patient scanned in a CT imager 10 or an x-ray imager (20). In the present example, in one embodiment, an imaged heart 102 is presented in a 3D-like view, for instance a volume rendered image, on a display 101, for instance a monitor, where a stenosed blood vessel 103 is visible on the display 101. In another embodiment a 2D image, for instance a 2D contrast-enhanced angiogram, of a part of the cardiac vasculatory system 202 is visualized on a display 201. Also here a stenosed blood vessel 203 is clearly present. For the accuracy of the proposed method, it is important to display the artery in an orientation that allows for an unobstructed view of the lesion. This is especially important in case of a 2D image. It may be necessary to obtain images from multiple angles and then manually or automatically select the best image.

Next, photographic image data is obtained 302 of the initial image data. The photographic image data is acquired by using a camera that is integrated in a portable mobile device 105, 205. The portable mobile device 105, 205 may be a smartphone, tablet computer, augmented reality glasses, a computer with a built-in or attached camera 106, 206, e.g. a computer equipped with a webcam or a laptop with an integrated webcam or any other portable mobile device that integrates an adequate computer processor and a camera. The camera 106, 206 may be a photo camera and/or a camera to capture moving images. The photographic image data should include at least a section 104, 204 that includes the part of the blood vessel 103, 203 that includes the stenosis, for instance the relevant part of the coronary tree. In the context of the present invention photographic data is not restricted to a single photographic image. It may also be a series of images, such as in a movie or a series of temporarily spaced sequential images. Recording of a series of images (heart beat in angiography, rotation in CT) allows improved vessel reconstruction if combined with suitable tracking. Alternatively, the application on the portable mobile device could simply select the frame with highest image quality or the best orientation to show the blood vessel and the stenosis.

The photographic image data may also include temporal information relating to a time frame in which the photographic data was obtained and/or positional information relating to a spatial position in which the photographic data was obtained. This data may be used as additional input in later-discussed algorithms and models to improve their accuracy and/or reliability.

The blood vessel and the stenosis are identified on the photographic image data by detecting 303 their contours 107, 207. The contours 107, 207 may be drawn manually by the user, or detected automatically, e.g. based on a vesselness filter. This part of the algorithm is the same as for FFR simulation based on 2D X-ray angiograms, and has been described in for instance, O. Wink, W. J. Niessen, M. A. Viergever, "Multi-scale vessel tracking", IEEE Transactions on Medical Imaging, vol. 23, no. 1, pp. 130-135, 2004.

Since the photographic image data is obtained using a portable mobile device, most likely held by a user, the distance between the display and the camera and/or the used zoom factor makes it difficult to assess the actual size of the blood vessel or stenosis. Therefore, it is essential to estimate 304 the blood vessel size to build a realistic model of the geometry of the area of interest. The estimation may be done by the user providing a scale factor 304-4 or by analyzing the photographic image data to detect known features 304-1. This may be done automatically or user-defined or user-assisted. The size of these known features may then be compared 304-2 and related to typical sizes and lengths of organs, such as the myocardium, bones, blood vessels and the like. For instance a database of known organ dimensions may be consulted. A scale factor may then be calculated 304-3 based on the compared dimensions of the known features and the imaged features. For more accuracy multiple features may be compared and a (weighted) average of a scale factor for each feature might be used.

Next a 3D artery model is reconstructed 305 from the photographic data using the detected contours and scale factor. Known algorithms may be used to reconstruct the 3D model from the 2D data. A 3D model may be built assuming a circular vessel cross section with the diameter obtained during the contour step (O. Wink, W. J. Niessen, M. A. Viergever, "Multi-scale vessel tracking", IEEE Transactions on Medical Imaging, vol. 23, no. 1, pp. 130-135, 2004), or using videodensitometry based methods (e.g., J. Haase et al., "Quantification of intracoronary volume by videodensitometry: Validation study using fluid filling of human coronary casts", Catheterization and Cardiovascular Diagnosis, vol. 33, no. 1, pp. 89-94, 1994).

In the next step blood pressure and blood flow values are simulated 306 proximal and distal to the stenosis using known algorithms, for instance as described in Van de Vosse, "Mathematical modelling of the cardiovascular system", Journal of Engineering Mathematics, vol. 47, pp. 175-183, 2003; Kim et al., "Patient-specific modeling of blood flow and pressure in human coronary arteries", Annals of Biomedical Engineering, vol. 38, no. 10, pp. 3195-3209; or Smith et al., "An anatomically based model of transient coronary blood flow in the heart", SIAM Journal on Applied Mathematics, vol. 62, no. 3, pp. 990-1018.

Also here the detected contours and scale factor need to be used as additional input in these algorithms. From the blood pressure and blood flow values a simulated FFR value is calculated 308.

The FFR values are then displayed 307 to the user, preferably on the display of the portable mobile device 105, 205. This may be done, for example, as a color coded gradient of pressure along the vessel 108, 208 and/or as a single value for a location distal to the stenosis 109, 209.

Other information may be displayed as well. For instance, a warning indication (e.g. visual or auditory) that an FFR value is below a certain threshold (e.g. 0.8), which would indicate that the stenosis is severe and treatment must be started. Additionally or alternatively, the user may be prompted to perform a more traditional non-invasive or invasive procedure if the values are below or near the threshold to obtain more, potentially improved, stenosis data.

The steps of capturing photographic data to simulating and displaying an FFR data may be embedded in software code loaded on the portable mobile device 105, 205, for instance in the form of an app or a computer program, or loaded on a remote workstation with which the portable mobile device, such as a mobile phone, is in wireless or wired contact.

While the invention has been illustrated and described in detail in the drawings and foregoing description, such illustration and description are to be considered illustrative or exemplary and not restrictive; the invention is not limited to the disclosed embodiments.

For instance, the invention is certainly not limited to the presented embodiments. For instance, the present invention would be suitable for any other initial image of a stenosed blood vessel obtained by any other suitable technique, for instance MR, PET, SPECT, Ultrasound or any other imaging modality that could provide an image suitable for use with this invention.

Furthermore, in addition to FFR simulations, other hemodynamic measures (e.g. CFR, HSR) or parameters like flow velocity or myocardial resistance could be extracted from the fluid dynamics simulations on the portable mobile device. To improve the simulation accuracy, the portable mobile device may capture additional measured values like aortic or distal pressure from the same or from other displays and include these measurements in the simulation.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method for obtaining stenosis information in a blood vessel comprising a stenosis, comprising:
   displaying an initial image of an area of interest of a patient comprising at least the stenosis;
   obtaining photographic data of the displayed initial image of the area of interest using a camera of a portable mobile device;
   estimating a blood vessel size from the photographic data;
   detecting contours of at least the blood vessel and the stenosis;
   reconstructing a blood vessel model based on the obtained photographic image data and the detected contours;
   simulating blood pressure values and blood flow values in the blood vessel proximal to and distal to the stenosis using at least the blood vessel model and the estimated blood vessel size;
   calculating a fractional flow reserve value from the simulated blood pressure values and blood flow values; and
   displaying the calculated fractional flow reserve value.

2. The method according to claim 1, wherein the initial image of the area of interest was obtained by 2D or 3D medical imaging data.

3. The method according to claim 1, wherein the blood vessel is displayed in an orientation such that an unobstructed view of the stenosis is displayed.

4. The method according to claim 1, wherein the photographic data comprises a still image or a series of still images.

5. The method according to claim 4, wherein the still image is manually or automatically selected from the series of still images.

6. The method according to claim 1, wherein the photographic data comprises at least one of 1) temporal information relating to a time frame in which the photographic data was obtained, 2) positional information relating to a spatial position in which the photographic data was obtained.

7. The method according to claim 1, wherein the blood vessel size is estimated by
    detecting known structures in the photographic image data;
    comparing the detected known structures to typical dimensions of the known structures; and
    calculating a scale factor based on the compared dimensions.

8. The method according to claim 1, wherein the blood vessel size is estimated or influenced by a user-defined scale factor.

9. The method according to claim 1, wherein the contours of the blood vessel and/or the stenosis are manually determined.

10. The method according to claim 1, wherein the contours of the blood vessel and/or the stenosis are automatically determined.

11. The method according to claim 1, wherein the calculated fractional flow reserve value are displayed as a single value distal to the stenosis or as a color coded pressure gradient along the blood vessel.

12. The method according to claim 1, wherein a recommendation for further investigation is displayed.

13. A portable mobile device, comprising:
    a camera for obtaining photographic image data from a displayed initial image data of at least a section of a blood vessel comprising a stenosis;
    a blood vessel size estimator for estimating a blood vessel size from the obtained photographic image data;
    a contour determiner for detecting a contour of the blood vessel contour and of the stenosis from the obtained photographic image data;
    a reconstructor for reconstructing a blood vessel model based on the obtained photographic image data and the detected contours;
    a simulator for simulating blood pressure values and blood flow values in the blood vessel proximal to and distal to the stenosis using at least the blood vessel model and the estimated blood vessel size;
    a calculator for calculating a fractional flow reserve value from the simulated blood pressure values and blood flow values; and
    a display for displaying the calculated fractional flow reserve value or a connection to an external display for displaying the calculated fractional flow reserve value.

14. The portable mobile device according to claim 10, wherein the portable mobile device is one of a mobile phone, a tablet computer, augmented reality glasses, a camera-equipped desktop, and laptop computer.

15. A non-transitory computer-readable medium having executable instructions stored thereon which, when executed by processing circuitry, cause the processing circuitry to perform a method for obtaining stenosis information in a blood vessel comprising a stenosis, the method comprising:
    obtaining, from a portable mobile device, photographic data of a displayed initial image data of at least a section of a blood vessel comprising a stenosis;
    estimating a blood vessel size from the obtained photographic image data;
    detecting a contour of the blood vessel contour and of the stenosis from the obtained photographic image data;
    simulating blood pressure values and blood flow values in the blood vessel proximal to and distal to the stenosis using at least the blood vessel model and the estimated blood vessel size;
    calculating a fractional flow reserve value from the simulated blood pressure values and blood flow values; and
    displaying the calculated fractional flow reserve value.

* * * * *